US010292645B2

United States Patent
Saitoh et al.

(10) Patent No.: US 10,292,645 B2
(45) Date of Patent: May 21, 2019

(54) INTRACEREBRAL CURRENT SIMULATION METHOD AND DEVICE THEREOF, AND TRANSCRANIAL MAGNETIC STIMULATION SYSTEM INCLUDING INTRACEREBRAL CURRENT SIMULATION DEVICE

(71) Applicants: The University of Tokyo, Tokyo (JP); OSAKA UNIVERSITY, Suita-shi, Osaka (JP)

(72) Inventors: Youichi Saitoh, Ikeda (JP); Masaki Sekino, Tokyo (JP); Yoshihiro Takiyama, Tokyo (JP); Keita Yamamoto, Tokyo (JP)

(73) Assignees: THE UNIVERSITY OF TOKYO, Tokyo (JP); OSAKA UNIVERSITY, Osaka (JP)

( * ) Notice: Subject to any disclaimer, the term of this patent is extended or adjusted under 35 U.S.C. 154(b) by 140 days.

(21) Appl. No.: 15/118,704

(22) PCT Filed: Feb. 6, 2015

(86) PCT No.: PCT/JP2015/053390
§ 371 (c)(1),
(2) Date: Aug. 12, 2016

(87) PCT Pub. No.: WO2015/122369
PCT Pub. Date: Aug. 20, 2015

(65) Prior Publication Data
US 2017/0049387 A1      Feb. 23, 2017

(30) Foreign Application Priority Data
Feb. 14, 2014   (JP) .................................. 2014-026927

(51) Int. Cl.
*A61B 5/00*      (2006.01)
*G06T 15/08*    (2011.01)
(Continued)

(52) U.S. Cl.
CPC ............ *A61B 5/4848* (2013.01); *A61B 5/055* (2013.01); *A61B 5/4064* (2013.01); *A61B 5/742* (2013.01);
(Continued)

(58) Field of Classification Search
CPC ..... A61B 5/055; A61B 5/4064; A61B 5/4848; A61B 5/742; A61N 2/006; A61N 2/02; G06T 15/08; G06T 2210/41
See application file for complete search history.

(56) References Cited

U.S. PATENT DOCUMENTS

| 2003/0004392 A1 | 1/2003 | Tanner et al. |
| 2003/0073899 A1 | 4/2003 | Ruohonen et al. |

(Continued)

FOREIGN PATENT DOCUMENTS

| CN | 101866485 A   | 10/2010 |
| JP | 2003-180649 A | 7/2003  |

(Continued)

OTHER PUBLICATIONS

Toschi N, Welt T, Guerrisi M, Keck M. A reconstruction of the conductive phenomena elicited by transcranial magnetic stimulation in heterogeneous brain tissue. Physica Medica (2008) 24, 80-86.*

(Continued)

*Primary Examiner* — Christine H Matthews
*Assistant Examiner* — Joshua Daryl D Lannu
(74) *Attorney, Agent, or Firm* — Sughrue Mion, PLLC

(57) ABSTRACT

An intracerebral current simulation method including a first step of providing head image data; a second step of forming a three-dimensional brain model including micro-polyhedron units; a third step of providing first information which includes conditions under which a coil is placed on a patient's head, an electric current is applied to the coil, and the patient's reaction to the magnetic stimulation is (Continued)

observed, the conditions including a position and orientation of the coil, an electric current applied to the coil, and a structure relating to a generated magnetic field of the coil; and a fourth step of calculating an eddy current or electric field induced inside each of the micro-polyhedron units on the basis of the first information provided in the third step and second information which includes conductivity assigned to each micro-polyhedron unit. Also disclosed is a transcranial magnetic stimulation device and system.

23 Claims, 19 Drawing Sheets

(51) Int. Cl.
*A61N 2/02* (2006.01)
*A61B 5/055* (2006.01)
*A61N 2/00* (2006.01)
*G06F 19/00* (2018.01)
*G16H 50/50* (2018.01)
*A61B 34/10* (2016.01)

(52) U.S. Cl.
CPC .............. *A61N 2/006* (2013.01); *A61N 2/02* (2013.01); *G06F 19/00* (2013.01); *G06T 15/08* (2013.01); *G16H 50/50* (2018.01); *A61B 34/10* (2016.02); *G06T 2210/41* (2013.01)

(56) References Cited

U.S. PATENT DOCUMENTS

| | | | |
|---|---|---|---|
| 2004/0039279 | A1 | 2/2004 | Ruohonen |
| 2005/0033380 | A1 | 2/2005 | Tanner et al. |
| 2005/0256539 | A1 | 11/2005 | George et al. |
| 2008/0161636 | A1* | 7/2008 | Hurme ............... A61N 2/02 600/13 |
| 2010/0113863 | A1 | 5/2010 | George et al. |
| 2012/0157752 | A1 | 6/2012 | Nishikawa et al. |
| 2013/0345491 | A1 | 12/2013 | Saitoh et al. |

FOREIGN PATENT DOCUMENTS

| | | |
|---|---|---|
| JP | 2004-000636 A | 1/2004 |
| JP | 2004-511314 A | 4/2004 |
| JP | 2006-255314 A | 9/2006 |
| JP | 2009-536073 A | 10/2009 |
| JP | 2012-125546 A | 7/2012 |
| WO | 02/32504 A2 | 4/2002 |
| WO | 2007/130308 A2 | 11/2007 |
| WO | 2010/147064 A1 | 12/2010 |
| WO | 2012/121341 A1 | 9/2012 |

OTHER PUBLICATIONS

International Preliminary Report on Patentability issued from the International Bureau in counterpart International Application No. PCT/JP2015/053390, dated Aug. 25, 2016.
Communication dated Oct. 12, 2017 from the European Patent Office in counterpart European application No. 15749544.1.
Dawson, T., et al., "Comparison of Magnetically Induced ELF Fields in Humans Computed by FDTD and Scalar Potential FD Codes", ANTEM, 1996, pp. 443-446 (4 pages).
Toschi, N., et al., "A reconstruction of the conductive phenomena elicited by transcranial magnetic stimulation in heterogeneous brain tissue", Physica Medica, 2008, vol. 24, pp. 80-86 (7 pages).
Barchanski, A., et al., "Large-Scale Calculation of Low-Frequency-Induced Currents in High-Resolution Human Body Models", IEEE Transactions on Magnetics, Apr. 2007, vol. 43, No. 4, pp. 1693-1696 (4 pages).
Thielscher, A., et al., "Impact of the gyral geometry on the electric field induced by transcranial magnetic stimulation", NeuroImage 54, 2011, pp. 234-243 (10 pages).
Dawson, T., et al., "Analytic Validation of a Three-Dimensional Scalar-Potential Finite-Difference Code for Low-Frequency Magnetic Induction", Applied Computational Electromagnetics Society Journal, Nov. 1996, vol. 11, No. 3, pp. 72-81 (10 pages).
Windhoff, M., et al., "Electric Field Calculations in Brain Stimulation Based on Finite Elements: An Optimized Processing Pipeline for the Generation and Usage of Accurate Individual Head Models", Human Brain Mapping, 2013, vol. 34, pp. 923-935 (13 pages).
International Search Report of PCT/JP2015/053390 dated Mar. 24, 2015.

* cited by examiner

MRI DATA OF BRAIN

MODEL INCLUDING ONLY GREY MATTER, WHITE MATTER,
AND CEREBROSPINAL FLUID

Fig.8
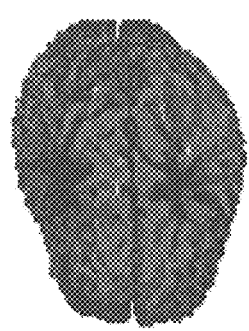
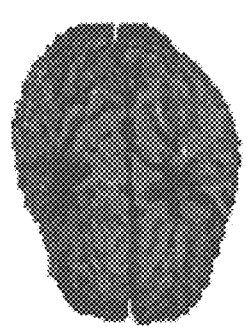
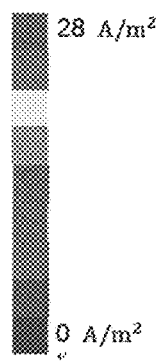
ANALYSIS RESULT FOR
ALL BIOLOGICAL TISSUES
ANALYSIS RESULT FOR
GREY MATTER,
WHITE MATTER, AND
CEREBROSPINAL FLUID

STIMULATION THRESHOLD AT LOCATIONS DISPLACED FROM OPTIMUM POSITION

EDDY CURRENT DISTRIBUTIONS WHEN STIMULATING OPTIMUM
STIMULATION POSITION (LEFT) AND POSITION AT DISTANCE OF
ABOUT 20 mm (RIGHT). BLACK CIRCLES REPRESENT RANGE OF
RADIUS 5 mm IN WHICH AVERAGE EDDY CURRENT DENSITY IS OBTAINED

CHANGE IN ANALYSIS RESULT CORRESPONDING TO
RADIUS OF REGION OF INTEREST

EDDY CURRENT DISTRIBUTION IN BRAIN

ANALYSIS RESULT WHEN STIMULATING LEFT
PREFRONTAL AREA LATERODORSAL SIDE

DIAGRAM OF THREE-DIMENSIONAL MODEL OF BRAIN, COIL WINDING SHAPE, AND COIL POSITION

INTRACEREBRAL CURRENT SIMULATION METHOD AND DEVICE THEREOF, AND TRANSCRANIAL MAGNETIC STIMULATION SYSTEM INCLUDING INTRACEREBRAL CURRENT SIMULATION DEVICE

CROSS REFERENCE TO RELATED APPLICATIONS

This application is a National Stage of International Application No. PCT/JP2015/053390 filed Feb. 6, 2015, claiming priority based on Japanese Patent Application No. 2014-026927 filed Feb. 14, 2014, the contents of all of which are incorporated herein by reference in their entirety.

TECHNICAL FIELD

The present invention relates to a method and a device for simulating an electric current or an electric field induced into the brain. The present invention also relates to a transcranial magnetic stimulation system having the device incorporated therein.

BACKGROUND ART

A transcranial magnetic stimulation is a technique of stimulating neurons by inducing an eddy current or an electric field in the brain through electromagnetic induction. In this technique, as shown in FIGS. 1 and 2, a current (e.g., alternating current) is applied to a stimulation coil placed on the skin of the head to form a variable magnetic field and to induce an eddy current or an electric field in the direction opposite to the coil current in the brain under the effect of the variable magnetic field, and an action potential is generated by stimulating the neurons with the eddy current or the electric field.

FIG. 3 shows an example of a stimulation coil drive circuit. In a principle of generating a momentary current in a coil, first, an electric charge is stored from a power source (including an alternating-current power source, a power circuit, and a booster circuit) into a capacitor. Subsequently, a thyristor is turned on to apply a current to a stimulation coil. The current is applied to a resonance circuit of the stimulation coil and the capacitor through a diode, and the thyristor is then turned off. As a result, a current corresponding to one cycle of a sine wave shown in FIG. 4 is applied to the stimulation coil.

The transcranial magnetic stimulation is used in clinical examinations and neuroscience including measurement of nerve conduction velocity.

In recent years, magnetic stimulation is gathering attention as therapeutic application to neuropathic pain, Parkinson's disease, depression, etc. A drug therapy may not effective to these diseases in some cases and methods of treatment in such a case include applying an electrical stimulation to the brain by implanting an electrode into the brain. However, this method requires a craniotomy and is therefore often not desired by patients. Thus, a repetitive transcranial magnetic stimulation performed by repeatedly applying a non-invasive magnetic stimulation not requiring a surgical operation is being studied as a method of treatment. For example, it is reported that a pain-relieving effect to intractable neuropathic pain is produced for about one day after magnetic stimulation to the primary motor cortex.

However, a conventional magnetic stimulation device weighs about 70 Kg and is available only in well-equipped medical institutions because electrical work is required for installation. Additionally, since a stimulation position is determined while referring to patient's MRI data during actual treatment, the treatment must be performed by a skilled health-care professional. In the treatment of intractable neuropathic pain, a coil is positioned on the target primary motor cortex with accuracy of 1 mm. However, to continuously acquire the pain-relieving effect, a patient must go to a medical institution every day. Therefore, a new magnetic stimulation device for home treatment shown in FIG. 5 has been developed that only requires an operation by a non-healthcare professional for utilization.

PRIOR ART DOCUMENTS

Patent Documents

The present inventors have developed the magnetic stimulation device shown in FIG. 5 and have already made patent applications of an improved figure-eight type magnetic field generation coil and positioning (WO2010/147064, Japanese Laid-Open Patent Publication No. 2012-125546).

SUMMARY OF THE INVENTION

Problem to be Solved by the Invention

A transcranial magnetic stimulation therapy includes stimulating neurons with an eddy current induced at a target site in the brain.

It is considered that the intensity and distribution of this eddy current are determined depending on a structure and characteristics of a coil, a magnetic field generation performance of an applied current etc., and a position of the coil relative to a patient.

However, it is not practical to measure an eddy current actually induced in the brain of a treated patient during magnetic therapy by using an electrode etc.

Therefore, attempts are made to analyze the eddy current induced in the brain through simulation from a magnetic field distribution generated by a coil.

The past intracerebral eddy current distribution simulation is performed as a calculation using a standard model and a current distribution is obtained by considering the brain as a uniform conductor.

However, since the actual brain is different in size and shape for each individual patient and has tissues different in electric conductivity, it is a problem that a current intensity distribution of an individual patient is difficult to calculate while a simulation calculation itself is complicated and requires time.

Means for Solving Problem

It is therefore an object of the present invention to establish a method and a device for simulating a magnitude and a distribution of an eddy current induced in the brain of a patient to be subjected to a transcranial magnetic stimulation treatment with accuracy extremely close to an actual measurement value by using a technique of modeling a brain model acquired by extracting a brain shape from tomographic images of an individual patient as well as a coil so as to determine a positional relationship between an arbitrary brain model and the coil before performing an eddy current analysis.

In this technique, preferably, a scalar potential finite difference method (hereinafter referred to as the "SPFD method") is used for an electromagnetic field analysis.

This technique enables observation of a current intensity distribution associated with a device position of a stimulation coil through a simulation and enables verification of a stimulation intensity, an eddy current intensity at a stimulation site, and an optimum position of the coil relative to a site desired to be stimulated, without actually applying a stimulation.

Since the use of the SPFD method shortens the considerable amount of time as compared to a conventional finite element method, this enables physicians to efficiently conduct studies and treatments.

Moreover, since a coil with optimum induced current distribution can easily be selected depending on a disease, this technique has a large significance in terms of medical treatment.

For analysis of intracerebral eddy current distribution, the SPFD method was used rather than the finite element method used in commercially available eddy current analysis software, and a solid to be analyzed including the brain is divided into minute polyhedral units (e.g., cubes) of minute elements, so as to obtain an eddy current induced in each of the minute polyhedral units. Software (program) for analysis using the SPFD method was uniquely developed.

Although other simulation calculation methods such as the finite element method may obviously be used for implementing the present invention, the original software using the SPFD method has the following three advantages.

The first advantages is that although the number of elements of a division model is limited to about one million in commercially available software using the finite element method, the original software has no limitation on the number of elements. Since the division number and a voxel size can arbitrarily be specified, the model can more finely be divided, and the analysis can finely be conducted. The second advantage is the absence of the need for creating an air layer. Although the air layer must be created around a brain model in accordance with meshes of the brain model in the commercially available software, since only the brain model is created, the present invention considerably reduces the time required for creating a model for analysis. The third advantage is that since the calculation technique is changed, a calculation time is reduced to about 1/20 of that of the commercially available software.

Details of the SPFD method used for analysis will hereinafter be described.

From the Faraday's law, an electric field E induced in the brain and an external magnetic flux density B satisfy Eq. (1).

[Eq. 1]

$$\nabla \times E = -\frac{\partial B}{\partial t} \quad (1)$$

If a magnetic vector potential A and an electric scalar potential $\varphi$ are selected to satisfy Eqs. (2) and (3), an electric field and a magnetic field acquired from these potentials satisfy Eq. (1).

[Eq. 2]

$$B = \nabla \times A \quad (2)$$

[Eq. 3]

$$E = -\frac{\partial A}{\partial t} - \nabla \phi \quad (3)$$

The total electric field E of Eq. (3) can be factorized into an electric field $E_1$ derived from a vector potential and an electric field $E_2$ derived from a scalar potential as described in Eqs. (4) to (6).

$$E = E_1 + E_2 \quad (4)$$

$$E_1 = -\frac{\partial A}{\partial t} \quad (5)$$
$$= -\frac{\mu_0}{4\pi} \frac{\partial}{\partial t} \int \frac{I(r')}{|r - r'|} dr'$$

$$E_2 = -\nabla \phi \quad (6)$$

In Eq. (5), deformation from a first line to a second line is in accordance with the Biot-Savart's law. In the equation, $\mu_0$ is a magnetic permeability of a vacuum; r is a position vector of a space; r' is a position vector on a magnetic field generation coil; and I(r') is a coil current at a position r'. The electric field $E_1$ derived from the vector potential is determined only by a winding shape of a coil and a current and can comparatively easily calculated by using Eq. (5). The magnetic field $E_2$ derived from the scalar potential is dependent on a head shape of a subject, and an advanced numerical analysis technique such as the SPFD method and the finite element method is required for obtaining this magnetic field. The advanced numerical analysis technique is also required for obtaining the total electric field E.

By substituting Eq. (3) and Eq. (7) of the Ohm's law into Eq. (8) of current continuity, Eq. (9) is obtained.

$$J = \sigma E \quad (7)$$

$$\nabla \cdot J = 0 \quad (8)$$

$$-\nabla(\nabla \sigma \phi)\nabla\left(\sigma \frac{\partial A}{\partial t}\right) \quad (9)$$

In Eq. (7), J is an induced current density, and $\sigma$ is an electric conductivity of a living body.

Discretization of Eq. (9) at contact points shared by eight minute polyhedral units turns Eq. (9) into Eq. (10).

$$\sum_{n=1}^{6} S_n \phi_n - \left(\sum_{n=1}^{6} S_n\right)\phi_0 = \sum_{n=1}^{6} (-1)^n S_n l_n \frac{\partial A_n}{\partial t} \quad (10)$$

In Eq. (10), $\varphi_n$ is an electric scalar potential at a contact point n; $A_n$ is a value at the center of a side in a component of an external magnetic vector potential parallel to a side n of a voxel connecting a contact point 0 and a contact point n; $l_n$ is the length of the side n; and $S_n$ is the conductance of the side n.

The electric scalar potential was obtained by applying Eq. (11) to Eq. (10), where $a_n$ is an area of a surface of a rectangular parallelepiped perpendicular to the side n and $\sigma_n$ is an average electric conductivity of four rectangular parallelepipeds in contact with the side n, and by solving the equations. Based on the obtained electric scalar potential, an eddy current density was obtained by using Eqs. (3) and (7).

$$S_n = \frac{\sigma_n a_n}{l_n} \quad (11)$$

As described above, in this simulation method, the SPFD method can be utilized to analyze both the total electric field E and the eddy current density J dependent on a head shape of a subject. The electric field E1 determined by a winding shape of a coil and a current can also be obtained in the course of the analysis.

To verify the accuracy of calculation according to the SPFD method, the present inventors performed a simulation of an eddy current induced by a superposed figure-eight coil for each of a sphere model of 75 mm in radius shown in FIG. 21A and a cube model of 120 mm in side length shown in FIG. 21B. The "superposed figure-eight coil" is a coil having two spiral coils arranged into a figure-eight such that the coils partially overlap with each other at respective end parts.

The sphere model ant the cube model were used so as to check whether an influence (such as an error) from geometrical properties of a simulation object exists due to a difference in calculation algorithm (concept of modeling) between the finite element method and the SPFD method.

For the coil at a position 1 cm away from a model surface, a current was set to 5.3 kA and 3.4 kHz. As can be seen from a result in the sphere model shown in FIG. 22A and a result in the cube model shown in FIG. 22B, it was confirmed that, as compared to the calculation result from the finite element method, an average induced current amount of elements included in a sphere within a constant length from a model surface part is calculated substantially without a difference even in the calculation result from the SPFD method.

In this analysis, out of head MRI data (image data) of each individual, only the image data of the grey matter, the white matter, and the cerebrospinal fluid were extracted for the analysis. FIG. 7 shows a model acquired by extracting the three brain tissues of the grey matter, the white matter, and the cerebrospinal fluid from the MRI data of the brain as shown in FIG. 6. Blue, green, and red represent the grey matter, the white matter, and the cerebrospinal fluid, respectively. FIG. 8 shows analysis results of eddy current density of the grey matter surface when electrical stimulations are applied under the same conditions to a model covering all the biological tissues such as the skins and muscles and a model acquired by extracting only the three elements of the grey matter, the white matter, and the cerebrospinal fluid, by actually using a numerical human body model. As shown, it can be seen that the two models have no significant difference in current density and have the same distribution of eddy current density. From the above, it was found that the analysis conducted by extracting only the grey matter, the white matter, and the cerebrospinal fluid is effective.

For brain shapes of individual patients, an analysis was conducted in terms of a current density in the primary motor cortex when an electrical stimulation at the same level as a motor threshold at an optimum stimulation position on the primary motor cortex is applied around the optimum stimulation position. The motor threshold as used herein refers to a magnetic field intensity at which a reaction of muscle is recognized with the probability of 50% or more when a magnetic stimulation is applied to the brain with a coil placed at the optimum stimulation position of a subject. Specifically, MRI images of the heads were acquired from a plurality of subjects and a coil was placed at the optimum stimulation positions of the subjects to examine the motor threshold. In this experiment, 10-turn figure-eight coils of 25 mm in inner diameter, 97 mm in outer diameter, and 6 mm in height and the pulse width of 280 µs were used. The coil was placed at 30 positions inside an elliptical region having a radius of about 25 mm from left to right (in a direction along the central sulcus) and a radius of about 15 mm from front to back (in a direction perpendicular to the central sulcus) around the optimum stimulation position to record the motor threshold and the three-dimensional position information of the coil corresponding to the MRI data at each place. Subsequently, an average eddy current density in 5 mm around the optimum stimulation position was calculated when the stimulation was applied to the brain at the same level as the motor threshold. Additionally, the motor thresholds were examined at the optimum stimulation position and several positions within the elliptical region described above.

FIG. 9 shows results of the analysis conducted for six subjects. The results represent distributions of the eddy current J and the electric field E on the grey matter surface when the coil is placed at the optimum positions on the six subjects to apply the stimulation corresponding to the motor threshold. As represented by Eq. (7), the eddy current and the electric field are in a proportional relationship. A color scale of the analysis results is the same for all the subjects. From these results, it is seen that a high current density appears also at positions around the primary motor cortex and that the current density corresponding to the stimulation threshold of the primary motor cortex varies depending on a subject. Table 1 shows results of the average eddy current density in the radius of 5 mm around a target site actually obtained from the analysis results of the six subjects. The brain tissues were excited at the eddy current density of 17.19 A/m$^2$ (the average value of the subjects). It was found that the intracerebral eddy current density corresponding to the stimulation threshold varies depending on a subject.

TABLE 1

Average Eddy Current Density Analysis Results at Target Sites of Six Subjects

| Subjects | Average Eddy Current Density (A/m$^2$) |
|---|---|
| A | 10.45 |
| B | 11.96 |
| C | 27.97 |
| D | 20.25 |
| E | 9.92 |
| F | 22.57 |
| Average | 17.19 |
| Standard Deviation | 6.83 |

FIG. 10 is a graph showing a stimulation threshold (actual measurement value of voltage magnitude at which a reaction of muscle is recognized with the probability of 50% or more) when a coil is placed at a location deviating from the optimum stimulation position, by using the motor threshold at the optimum stimulation position as 100. In this result, as the coil deviated from the optimum stimulation position, a magnetic field stimulation intensity required for generating a twitch (muscle cramp, muscle twitch) became larger.

FIG. 11 shows a result of calculation according to a simulation method of the present invention in terms of difference in current density at the optimum stimulation position when the coil position is changed. The origin is set to the optimum stimulation position to show a "deviation (movement amount)" from the optimum stimulation position in the graph with the X-axis direction defined as a direction parallel to the central sulcus and the Y-axis defined as a direction perpendicular to the central sulcus. The optimum stimulation position and the "deviation" are actual measurement values, and the current density is an analytical value. From this figure, it was seen that a deviation of the coil position in the direction parallel to the central sulcus has a greater effect on the change in eddy current density at the optimum stimulation position as compared to the perpendicular direction and that the magnitude of the eddy current density is reduced by half in a place at a distance of 20 mm.

FIG. 12 shows the eddy current distributions of the brain in the cases of stimulating the optimum stimulation position and a position at a distance of 20 mm. It can be seen also from this figure that the deviation of 20 mm in the coil position generates a large difference in the intracerebral current distribution.

In addition to the form of using the simulation method according to the present invention to calculate the eddy current density distribution in the entire brain viewed from above or the eddy current density at a certain intracerebral position in the case of changing a position of a therapeutic coil as described above, the simulation method according to the present invention described above may additionally or independently be used for calculating the eddy current density distribution in the entire brain viewed from above or the eddy current density at a certain intracerebral position in the case of changing at least any of information on coil direction, information on coil applied current, and information on applied voltage. A specific configuration for calculating or displaying the simulation result in this way will be described separately.

It was found that a difference of several % exists in power source necessary for generating at the target site the eddy current density reaching the motor threshold when the coil is placed around the optimum stimulation position, between a value obtained from analysis results and an actually measured value. It is considered that the difference between the both values was caused because the eddy current density was obtained in a large region. Therefore, a difference from an actual measurement value was obtained for each subject in terms of a current slew rate (a slope of a rising current (or an increase in the current per unit time) when the current corresponding to one cycle of a sine wave is applied to a coil so as to induce a magnetic field) necessary for inducing an eddy current reaching the motor threshold at the target site when the coil is placed around the optimum stimulation position, in the case of changing a radius from 2 mm to 10 mm in a region of interest where the average eddy current density is obtained. The results are shown in FIG. 13. Curves represent respective subjects. From this figure, it was seen that the radius of the region of interest (region to be evaluated) has no effect on the results.

The intracerebral eddy current distribution (analysis result) is shown in FIG. 14. A dashed line of the figure represents the region of interest having the radius of 5 mm, and a larger eddy current is induced in a red portion. From this figure, it is seen that the region of interest includes not only a grey matter portion in which a large eddy current density is induced but also a portion in which the eddy current is less induced Therefore, it is considered that the difference between the actual measurement value and the analysis result can possibly be made smaller by comparing the results acquired by defining as the region of interest only the portion in which a large eddy current is induced when the coil is placed at the optimum position.

To determine conditions of the magnetic stimulation treatment for individual patents, it is required to stimulate the primary motor cortex and to obtain a threshold (motor threshold) at which a twitch (muscle cramp, muscle twitch) such as a motion of a finger occurs in response. However, the twitch does not appear in some patients even when a stimulation device is raised to the maximum power and, in such a case, the magnetic stimulation treatment cannot be performed. Additionally, an object to be stimulated may be a site other than the primary motor cortex depending on a disease and, since the twitch cannot be observed from a stimulation to such a site, the stimulation intensity must be determined with an indirect method. Application to such a patient is considered as an application example of the original software. For example, if no twitch is observed from stimulation to the primary motor cortex, a stimulation intensity can be presented by a computer simulation such that an average neuronal excitation threshold of 17.19 A/m$^2$ can be induced in the primary motor cortex. With regard to the treatment of depression, it is reported that a transcranial magnetic stimulation to the left DLPFC (dorsolateral prefrontal cortex) is effective. However, since the twitch cannot be observed from the stimulation to the prefrontal area, a stimulation is preliminarily applied to the motor area to obtain a magnetic field intensity corresponding to the motor threshold, and the treatment conditions in the prefrontal area are defined based on the magnetic field intensity. By using the software according to the present invention, the eddy current density induced in the prefrontal area can be estimated from analysis of the eddy current density and, therefore, the treatment conditions can be determined such that the eddy current to the prefrontal area is set to a proper value.

FIG. 15 shows an analysis result of the eddy current distribution when the left DLPFC (dorsolateral prefrontal cortex) is actually stimulated under the same condition as Table 1 (the current amplitude is 3431 A) in the brain model of the subject D of Table 1. A red frame in the figure shows an actually stimulated region. As is the case with the above analysis, this result shows the average eddy current density of 21.49 A/m$^2$ in the radius of 5 mm around the stimulation position. It can be understood from this result and Table 1 that applying the magnitude of 3233 A (see Eq. (8)) can induce the same eddy current as the eddy current density corresponding to the motor threshold in the motor area on left DLPFC (dorsolateral prefrontal cortex).

[Eq. 4]

$$3431 \times \frac{20.25}{21.49} = 3233 A \qquad (12)$$

Even when a stimulation is applied with the same magnetic field intensity, a different eddy current may be induced due to a change of the stimulation site. By evaluating the eddy current induced in an object site in advance through a simulation, a more proper stimulation intensity can possibly be set.

Description will hereinafter be made on an example in which the knowledge described above was confirmed by the simulation method according to the present invention.

FIG. 23A shows a head MRI image of the subject and an arrow indicates a stimulation position in the prefrontal area. When the induced current of the brain was calculated by the simulation method described above (it is noted that the radius of the sphere for calculating an average in the sphere was set to 10 mm) under the conditions of the stimulation position set to the primary motor cortex and the therapeutic coil current value set to 3430 A, a distribution shown in FIG. 23B was obtained. The average eddy current density at the stimulation position within the radius of 10 mm was 19.9 A/m$^2$.

When the same simulation was performed for the same subject under the same condition of the therapeutic coil current value set to 3430 A at the stimulation position set to the prefrontal area, the induced current of the brain has a distribution shown in FIG. 23C. The average eddy current density at the stimulation position within the radius of 10 mm was 17.6 A/m².

As described above, it can be seen that when the same subject is stimulated by the same coil current, different stimulation sites of the brain induce different eddy current distributions and different eddy current values at the stimulation sites.

Therefore, it can be inferred that, in the case of a currently typically performed method of, for example, setting the stimulation intensity to 110% or 120% based on RMT determined by the primary motor cortex stimulation, a stimulation may added to the prefrontal area with an intensity different from intended stimulation intensity.

From the above, by using an intracerebral induced current simulation technique of the present invention in advance for the object site other than the primary motor cortex, new stimulation intensity capable of contributing to treatment effectiveness can be considered.

<Introduction>

The transcranial magnetic stimulation (TMS) is one of techniques recently widely used as methods of treating neurological and psychiatric diseases. Particularly, the repetitive transcranial magnetic stimulation (rTMS) including intermittently applying more intense stimulations is known to have more clear effect of treatment. On the other hand, the transcranial magnetic stimulation has a problem that a stimulation intensity of a coil used for the transcranial magnetic stimulation is desired to be suppressed as small as possible so as to prevent unintended adverse effect and unnecessary heating of the coil.

For one approach to solve this problem, the present inventors focused attention on the fact that the presence of a "coil stimulation angle appropriate to each of subjects" is indicated in some studies in which the transcranial magnetic stimulation is actually performed.

In particular, the present inventors formed a hypothesis that if this optimum coil stimulation angle is clarified by an electromagnetic calculation before an operation of the transcranial magnetic stimulation, the stimulation can be applied by a smaller current and this can be a support for the operation.

From the following results of the studies by the present inventors, how the effect of the cerebrospinal fluid electromagnetically acts was revealed in a simplified transcranial magnetic stimulation model associated with the sulcus and the cerebrospinal fluid inside the sulcus. Based on these results, the present inventors newly established a method of calculating an appropriate stimulation angle at each of the stimulation sites of the brain with simplified calculation, which will be described below.

<Method>

The present inventors first created a simplified brain model including the sulcus shown in FIG. 24A and simulated the effect of the rotation angle of the transcranial magnetic stimulation coil relative to the sulcus. The brain model was made up of the grey matter with the electric conductivity of 0.11 S/m and the 2-mm-thick cerebrospinal fluid with the electric conductivity of 1.79 S/m and the sulcus was created to have the depth of 2 cm and the width of 2 mm. The stimulation coil has a figure-eight having the outer diameter of 5.1 cm and the inner diameter of 1.1 cm, and the current of 5.3 kA was applied thereto. The coil was fixed 1 cm above the brain model surface to apply stimulations at angles of 0 degrees, 30 degrees, 45 degrees, 60 degrees, and 90 degrees relative to the sulcus, and the results were compared by averaging induced currents of elements included in a sphere from the center point of the coil.

Subsequently, the present inventors formed brain shape data acquired as MRI images from a subject into three elements of the grey matter, the white matter, and the cerebrospinal fluid and performed a simulation of transcranial magnetic stimulation for the data. Additionally, the present inventors used the brain shape data based on MRI images to create a hollow model virtually composed only of the cerebrospinal fluid while having the same brain shape as the actual brain in terms of the sulcus etc., so as to perfume the same simulation. The magnetic stimulation coil was rotated from an initial stimulation direction by 10 degrees to 180 degrees, and comparison was made by calculating an average of induced currents of elements included in a sphere from the center point of the coil for each of the "grey matter+white matter" and the "cerebrospinal fluid" in the three-element model and the same average for the "cerebrospinal fluid" in the hollow model.

<Results>

In the simplified brain model shown in FIG. 24A, a relationship of inverse correlation (r=−0.99) was recognized in the induced currents in the grey matter and the cerebrospinal fluid. It may be considered that such a relationship is recognized because the cerebrospinal fluid is the substance having the highest electric conductivity in the head and generates a non-negligible coil loss. Particularly, when the coil was applied in parallel with the sulcus as shown in FIG. 24B, the stimulation intensity of the coil was reduced. Therefore, it can be inferred that the optimum coil stimulation direction is the direction perpendicular to the sulcus as shown in FIG. 24C.

In the above description of the geometric arrangement of the coil and the sulcus, the "coil in parallel with the sulcus" means that the principal flow direction of the eddy current induced by the coil is in parallel with the groove direction of the sulcus and, similarly, the "coil perpendicular to the sulcus" means that the principal flow direction of the eddy current induced by the coil is perpendicular to the groove direction of the sulcus.

Also in the simulation in the actual brain model shown in FIG. 25A generated from the MRI images of the subject (FIG. 25B shows a sphere for calculation of the average of induced currents), a relationship of inverse correlation (r=−0.79) was recognized also between the induced current of the grey matter/the white matter and the induced current of the cerebrospinal fluid, and changes in the induced currents were recognized in accordance with a stimulation angle (FIG. 25D).

Additionally, from the induced current in the cerebrospinal fluid in the hollow model as shown in FIG. 25C virtually composed only of the cerebrospinal fluid while having the actual brain shape derived from brain MRI images of a patient, a result was acquired that has substantially no difference from the eddy current induced in the cerebrospinal fluid in the three-element model (actual brain model) having the shape derived from the brain MRI images and composed of the grey matter, the white matter, and the cerebrospinal fluid (mean squared error=5.34 V/m). Therefore, it was found that the optimum coil stimulation angle can be inferred with sufficient accuracy even from a calculation using the hollow model and that a calculation amount can accordingly be reduced by 70% as compared to the case of using the three-element model.

It is considered that with the above technique, the neuronal excitation threshold can be estimated in a region other than the motor area.

Additionally, from the analysis of the intracerebral eddy current density distribution according to coil position deviations, it was confirmed that the intracerebral eddy current density changes due to a difference in coil position, which accordingly changes the motor threshold, and the anisotropy was found in the distribution of the intracerebral eddy current density. It is believed that the analysis of the intracerebral eddy current distribution must be advanced and that measurement at a position closer to the optimum stimulation position is required for measurement of the motor threshold.

The present invention was conceived based on the knowledge described above and an intracerebral current simulation method comprises a first step of providing head image data including at least a portion of a brain out of tomographic image data of a patient;

a second step of forming a three-dimensional brain model composed of respective minute polyhedral units acquired by dividing at least one region making up the brain of the head image data provided at the first step into minute elements;

a third step of providing first information including, out of conditions when a coil is placed on the head of the patient to apply a current to the coil to provide a magnetic stimulation to the brain of the patient and a patient's reaction to the magnetic stimulation is observed, at least conditions of a position and a direction of the coil, a condition of the current applied to the coil, and a condition of structure related to a formed magnetic field of the coil; and a fourth step of calculating eddy currents or electric fields induced in the respective minute polyhedral units of the three-dimensional brain model based on the first information provided at the third step and second information including an electric conductivity assigned to each of the minute polyhedral units.

According to the intracerebral current simulation method including such a configuration, since a model corresponding to a brain shape of an individual patient is formed and an intracerebral current is analyzed based on the model, the distribution of the eddy currents or electric fields induced in the actual brain can accurately be comprehended. Additionally, when the position of the coil deviates from the optimum stimulation position, the intracerebral eddy current distribution can more accurately be comprehended. By using an analysis result of the eddy current distribution or the electric field distribution, a transcranial magnetic stimulation system capable of more efficient stimulation of the brain can be designed.

The intracerebral current simulation method of the present invention in another form comprises a fifth step of visually displaying distribution of eddy currents or electric fields calculated at the fourth step. According to this method, the distribution of the intracerebral eddy currents or electric fields can visually be comprehended.

Preferably, the respective minute polyhedral units are assigned to have electric conductivities of any of the grey matter, the white matter, and the cerebrospinal fluid. Preferably, the first information includes at least a current value or a voltage value of the current. Preferably, the eddy currents or electric fields are calculated by a scalar potential finite difference method.

An intracerebral current simulation device and a transcranial magnetic stimulation system having the device incorporated therein according to the present invention comprises a first means providing head image data including at least a portion of a brain out of tomographic image data of a patient;

a second means forming a three-dimensional brain model composed of respective minute polyhedral units acquired by dividing at least one region making up the brain of the head image data provided by the first means into minute elements;

a third means providing first information including, out of conditions when a coil is placed on the head of the patient to apply a current to the coil to provide a magnetic stimulation to the brain of the patient and a patient's reaction to the magnetic stimulation is observed, at least conditions of a position and a direction of the coil, a condition of the current applied to the coil, and a condition of structure related to a formed magnetic field of the coil; and a fourth means calculating eddy currents or electric fields induced in the respective minute polyhedral units of the three-dimensional brain model based on the first information provided by the third means and second information including an electric conductivity assigned to each of the minute polyhedral units.

Preferably, the intracerebral current simulation device and the transcranial magnetic stimulation system comprise a fifth means visually displaying distribution of eddy currents or electric fields calculated by the fourth means.

An intracerebral current simulation device and a transcranial magnetic stimulation system having the device incorporated therein according to the present invention comprises a first means providing head image data including at least a portion of a brain out of tomographic image data of a patient;

a second means forming a three-dimensional brain model composed of respective minute polyhedral units acquired by dividing at least one region making up the brain of the head image data provided by the first means into minute elements;

a third means providing first information including, out of conditions when a coil is placed on the head of the patient to apply a current to the coil to provide a magnetic stimulation to the brain of the patient, at least conditions of a position and a direction of the coil, a condition of the current applied to the coil, and a condition of structure related to a formed magnetic field of the coil; and a fourth means calculating eddy currents or electric fields induced in the respective minute polyhedral units of the three-dimensional brain model based on the first information provided by the third means and second information including an electric conductivity assigned to each of the minute polyhedral units.

In the present invention, the current applied to the coil may be either an alternating current or a pulsating current.

As shown in FIG. 9, an eddy current and an electric field intensity induced in the brain by a magnetic field of a coil is in a proportional relationship. Therefore, in the description related to the present invention, it should be understood that "eddy current" can be replaced with "electric field" and that the contents after such a replacement also belong to the technical scope of the present invention.

BRIEF DESCRIPTION OF DRAWINGS

FIG. 8 is a diagram of an analysis result of an eddy current density on a grey matter surface when an electrical stimulation is applied to the model acquired by extracting the brain tissues of the grey matter, the white matter, and the cerebrospinal fluid of the human brain.

MODES FOR CARRYING OUT THE INVENTION

First Embodiment

Figure 16:
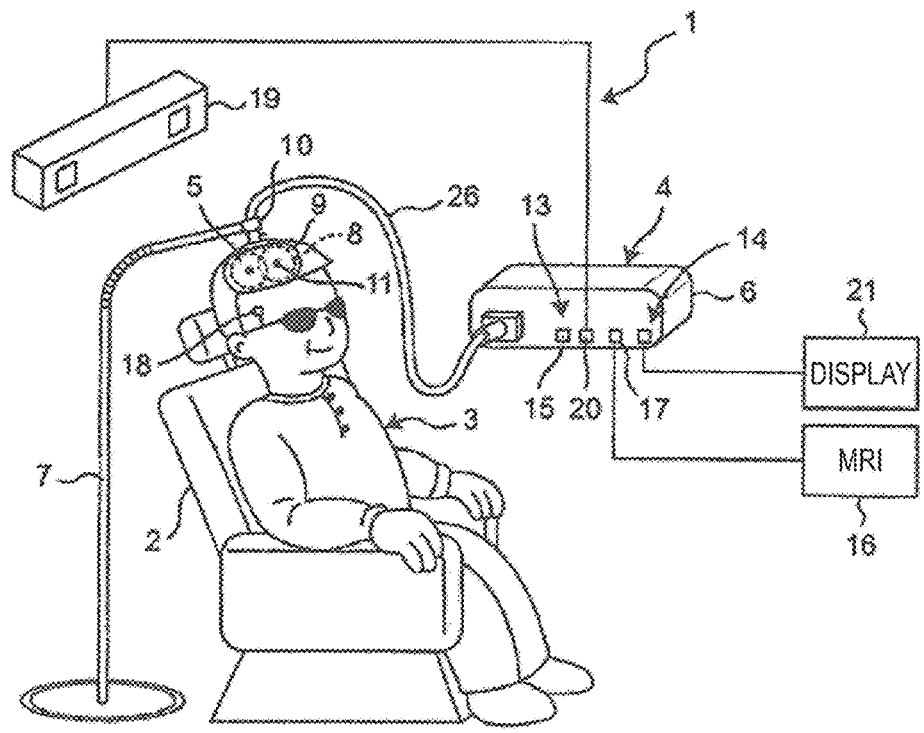
FIG. 16 is a schematic of a configuration of a transcranial magnetic stimulation system according to the present invention.

Referring to FIG. 16, a transcranial magnetic stimulation system (hereinafter simply referred to as the "system") 1 has a magnetic stimulation device 4 applying a magnetic stimulation to the brain of a patient 3 supported by a support mechanism (e.g., a chair 2 or a bed).

The magnetic stimulation device 4 has a coil unit (coil device) 5 and a control unit 6 so as to form a dynamic magnetic field applying the magnetic stimulation to the brain of the patient 3.

As shown, the coil unit 5 is preferably supported by a proper positioning unit 7 to enable free movement along a head surface of the patient 3 and positioning at an arbitrary position. The coil unit 5 includes the coil 8 and a casing 9 made of an electrical insulating material surrounding the coil 8. The casing 9 includes a holder 10 formed integrally with the casing 9 and is held via the holder 10 by the positioning unit 7. The coil 8 can be any known coil such as one cyclic coil and a figure-eight coil having conductive wires arranged into a figure-eight (e.g., a coil disclosed in Japanese Laid-Open Patent Publication No. 2012-125546). The casing 9 integrally includes three or more observation objects (e.g., marks 11 or targets such as protrusions). These observation objects are used for obtaining a position and a direction of the coil 8 relative to the patient's head.

The control unit 6 includes a box-shaped housing 12. The housing 12 includes an input part 13 and an output part 14.

The input part 13 includes a drive condition setting part 15 setting drive conditions of the system 1 (e.g., voltage, current, and frequency applied to the coil 8); a data receiving part 17 receiving human (particularly, head) tomographic image data generated by a tomographic imaging device (e.g., MRI, CT, PET)] 16; and a data receiving part 20 receiving image data from a stereo-imaging optical three-dimensional position sensing camera (hereinafter simply referred to as the "camera") 19 concurrently photographing the marks 11 disposed on the casing 9 of the coil unit 5 and three or more observation objects (e.g., marks 18 or protrusions) disposed on a wearing article (e.g., eyeglasses) such as eyeglasses worn by the patient 3 or the skin of the patient 3. Although not shown, the camera 19 is attached to the positioning unit 7 or a fixing part in a room housing the system 1.

It should be understood that in the present invention, the current applied to the coil includes not only a current having a flow direction periodically changing over time (alternating current) but also a current having a constant flow direction and a periodically varying magnitude (so-called "pulsating current").

The output part 14 is connected to a display 21 such as a liquid crystal display device or a computer (not shown) including a display and is configured such that data (e.g., image data) output from the control unit 6 can be output to the display 21 to display a corresponding image thereon.

Figure 17:
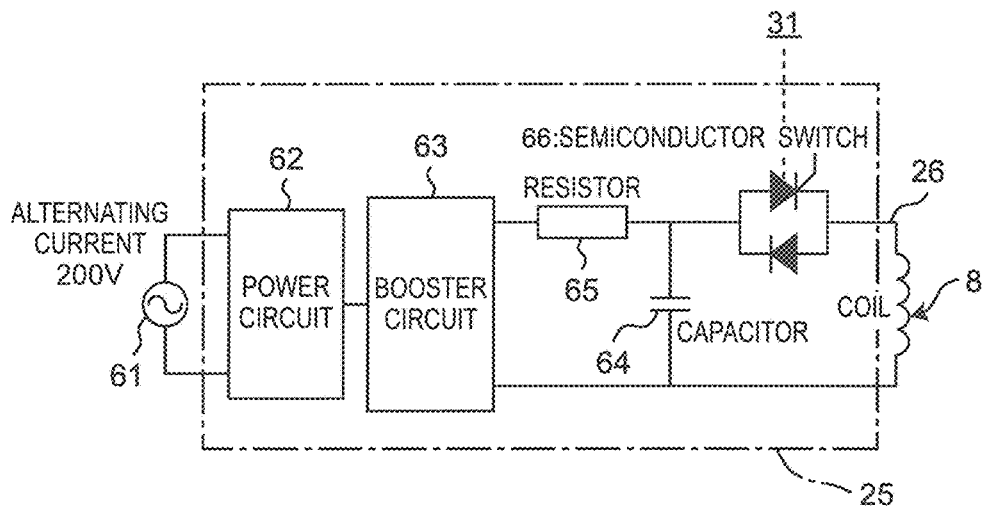
FIG. 17 is a diagram of a coil drive circuit incorporated in the system of FIG. 16.

A coil drive circuit 25 shown in FIG. 17 is housed inside the housing 12 and this coil drive circuit 25 is electrically connected through a cable 26 to the coil 8.

Figure 18:
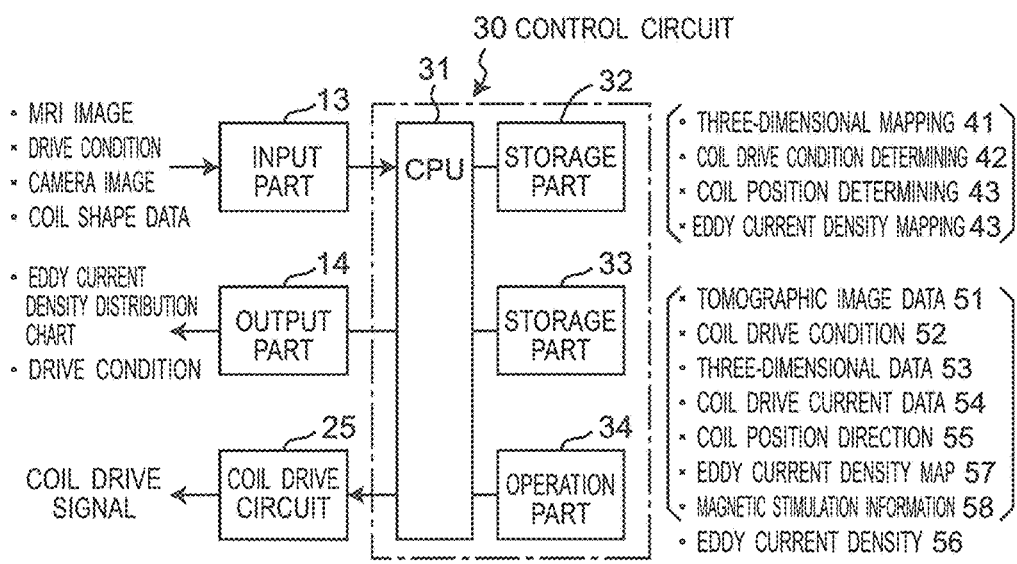
FIG. 18 is a diagram of a control circuit incorporated in the system of FIG. 16.

A control circuit 30 shown in FIG. 18 is also housed inside the housing 12. The control circuit 30 includes a central processing unit (hereinafter referred to as the "CPU") 31 as well as a first storage part 32, second storage part 33, and an operation part 34 connected to the CPU 31.

Figure 1:
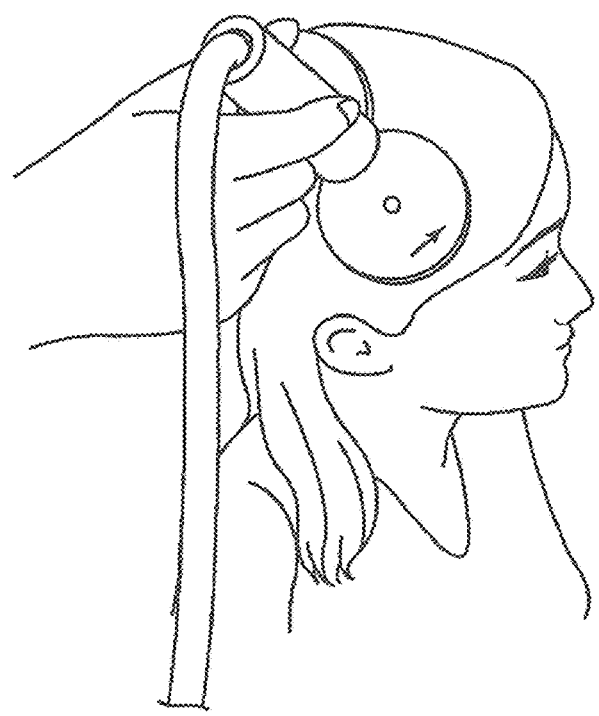
FIG. 1 is a diagram of a state of providing a magnetic stimulation treatment to a patient.
Figure 2:
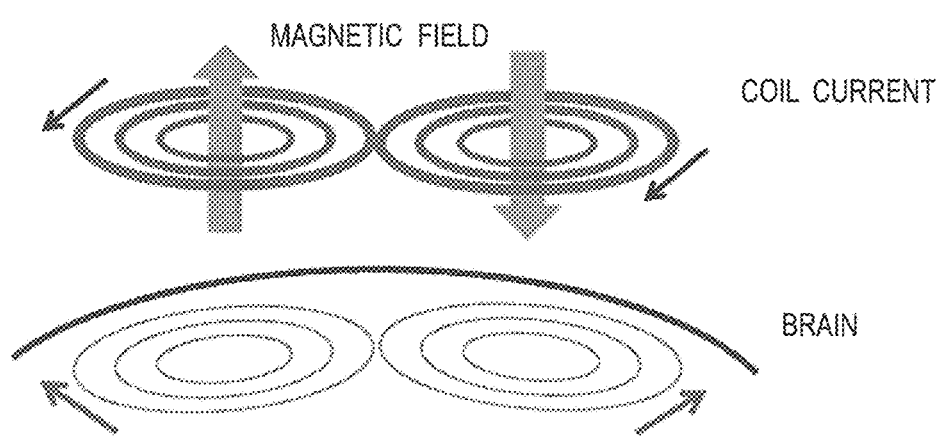
FIG. 2 is a diagram of an eddy current induced by a figure-eight coil.
Figure 3:
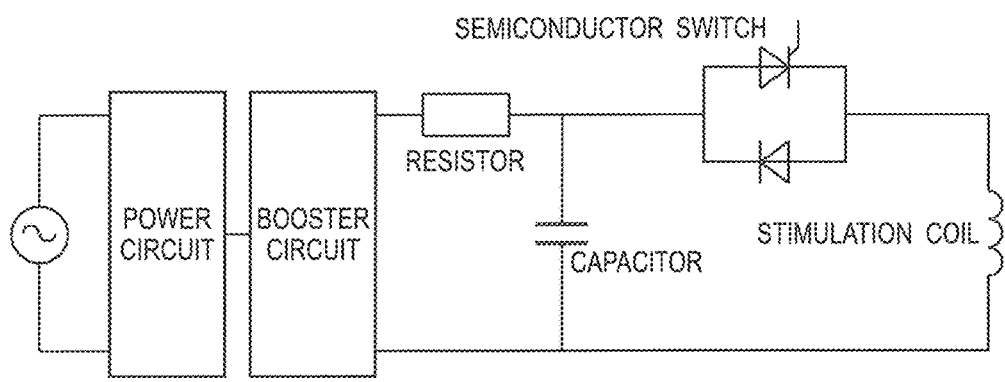
FIG. 3 is a diagram of a drive circuit applying a current to a coil.
Figure 4:
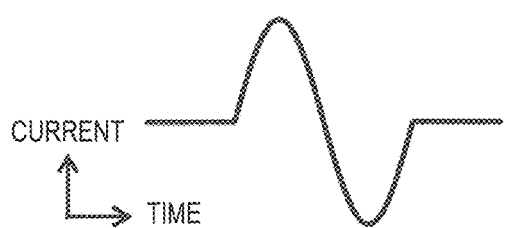
FIG. 4 is a diagram of a current waveform output from the drive circuit.
Figure 5:
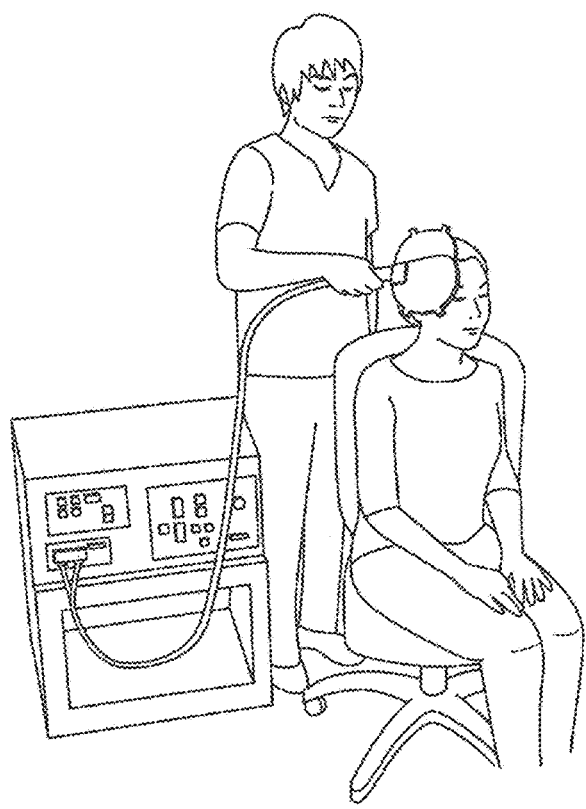
FIG. 5 is a diagram of a usage state of a magnetic stimulation device.
Figure 6:
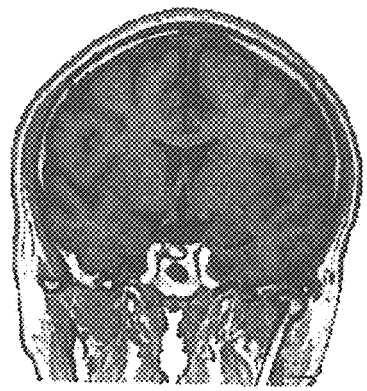
FIG. 6 is a diagram of MRI data of a human brain.
Figure 7:
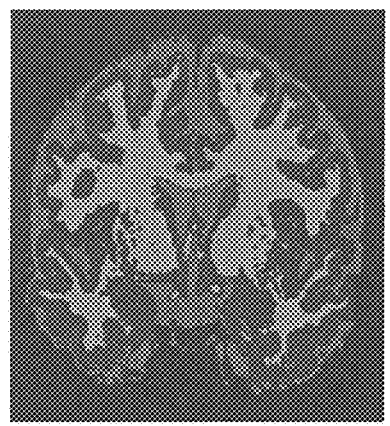
FIG. 7 is a diagram of a model acquired by extracting the brain tissues of the grey matter, the white matter, and the cerebrospinal fluid of the human brain.
Figure 9:
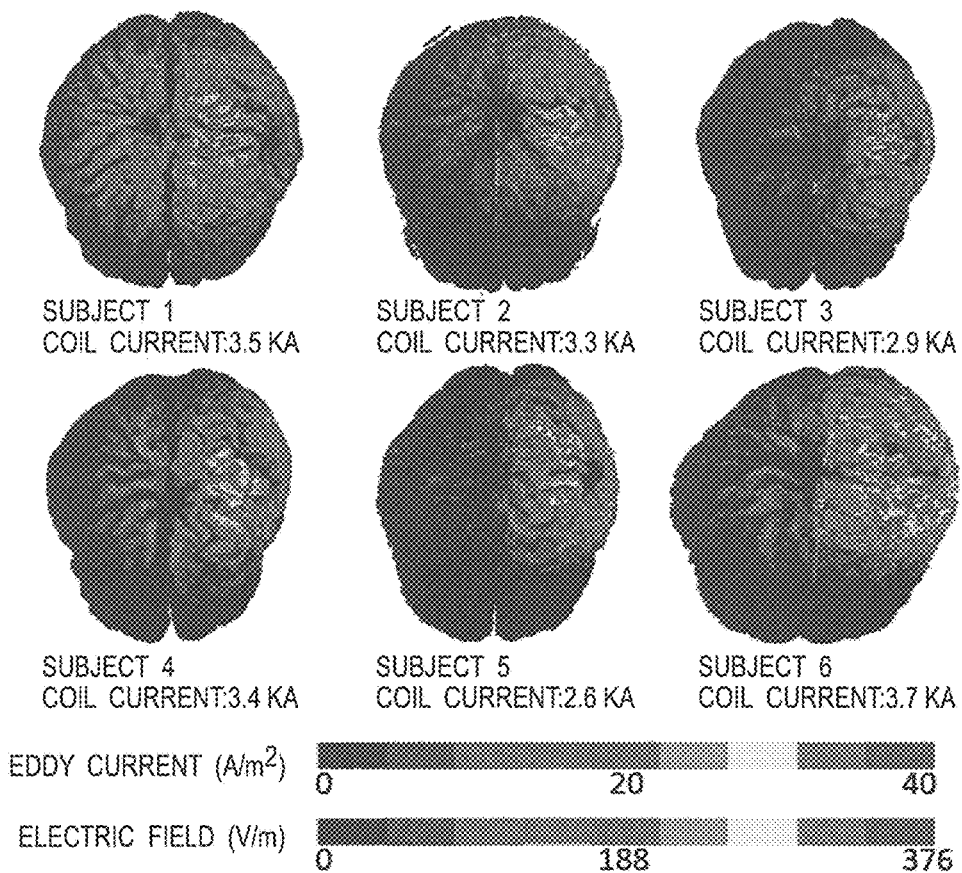
FIG. 9 is a diagram of current density on grey matter surfaces when a coil is placed at an optimum position and a stimulation corresponding to a motor threshold is applied to six subjects.
Figure 10:
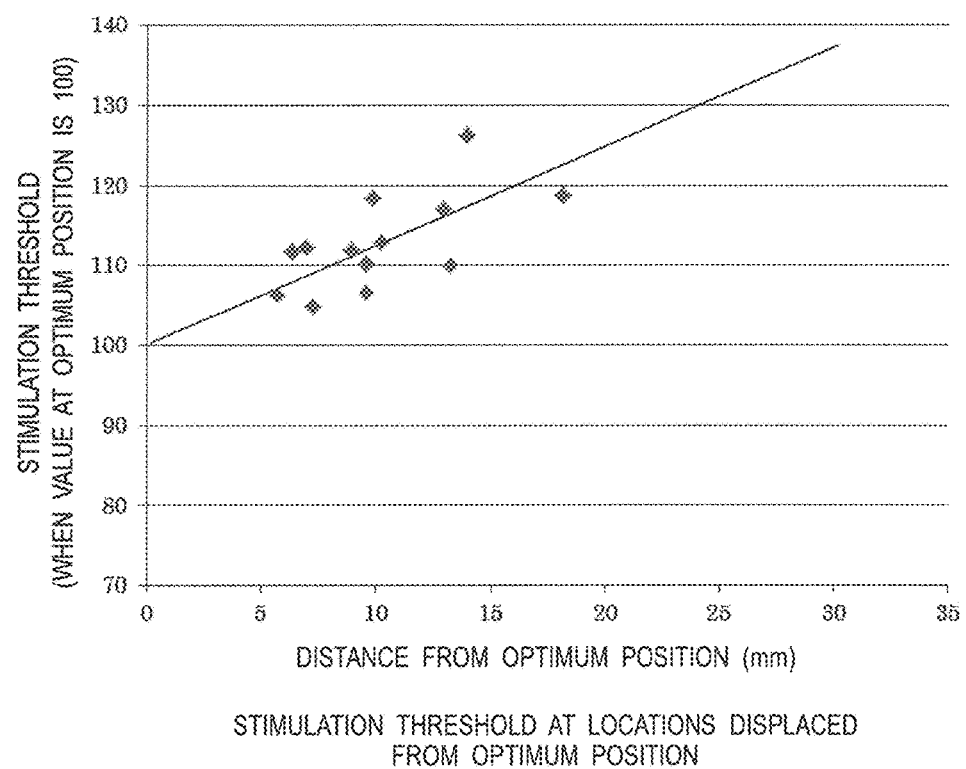
FIG. 10 is a graph showing actual measurement values of stimulation threshold when the coil is placed at a location moved from an optimum stimulation position, by using the motor threshold corresponding to the optimum stimulation position as 100.
Figure 11:
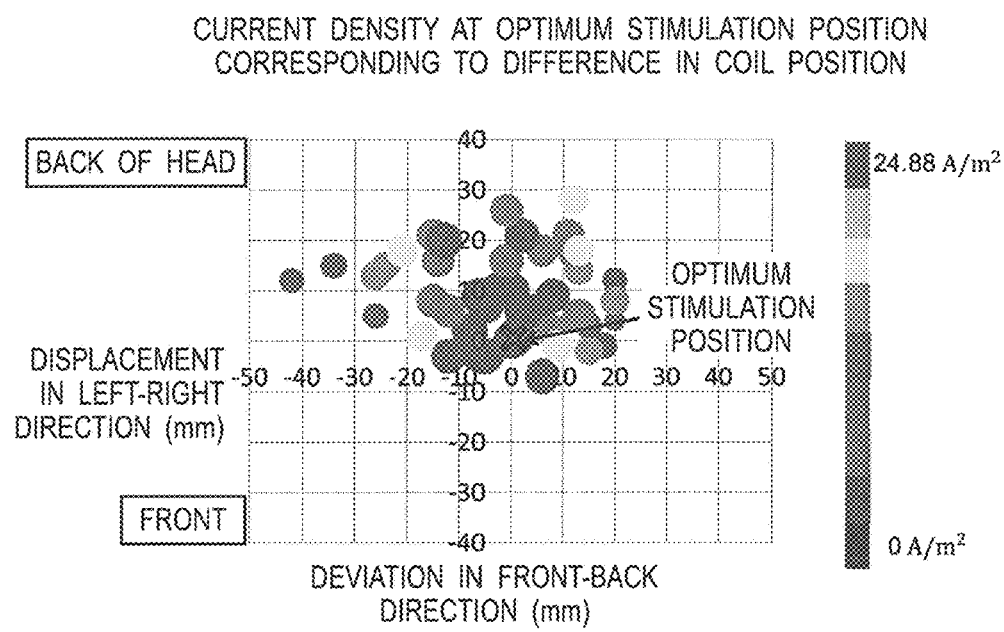
FIG. 11 is a diagram of current density at the optimum stimulation position when the coil position is changed.
Figure 12:
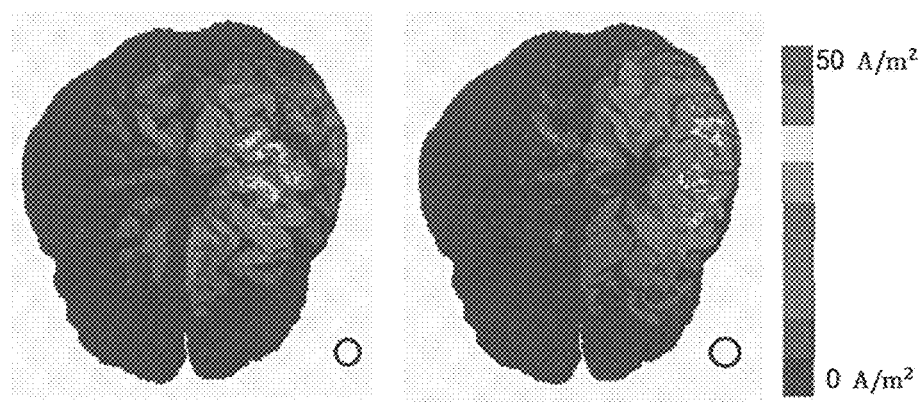
FIG. 12 is a diagram of distributions of intracerebral eddy currents in the cases of stimulating the optimum stimulation position and a position at a distance of 20 mm therefrom.
Figure 13:
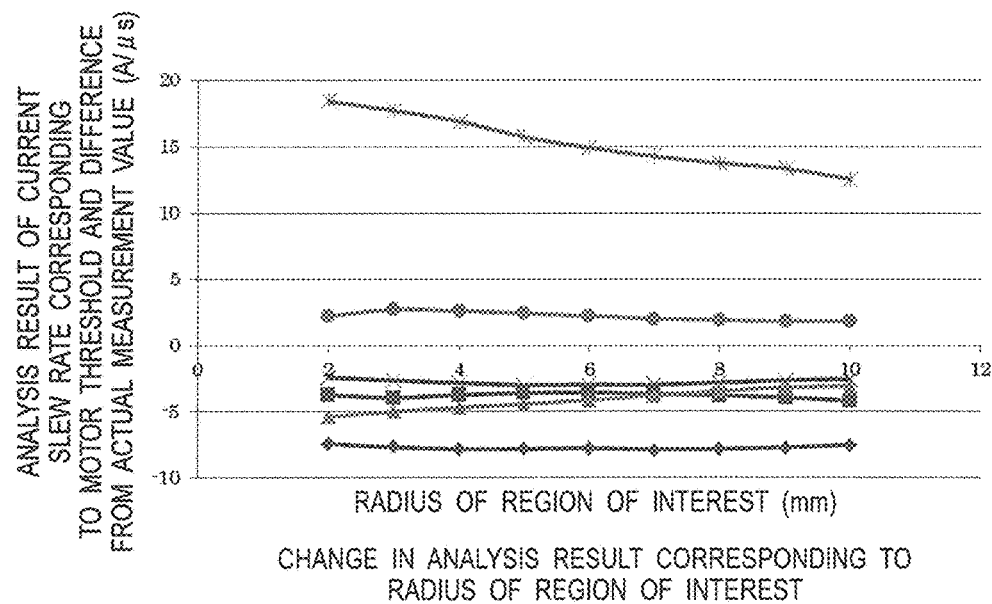
FIG. 13 is a diagram of difference between a current slew rate necessary for generating an eddy current reaching the motor threshold at the target site and an actual measurement value for each of the subjects when a region of interest for obtaining an average eddy current density is changed in radius.
Figure 14:
FIG. 14 is a diagram of an analysis result of the intracerebral eddy current distribution.

The first storage part 32 stores various pieces of software. For example, the various pieces of software include three-dimensional mapping software 41 creating a three-dimensional brain model (three-dimensional map) based on tomographic image data (e.g., medical mage processing software "Real INTAGE" commercially available from Cybernet Systems Co., Ltd.); coil drive condition determining software 42 determining a current applied to the coil based on a drive condition input through the input part 13; coil position determining software 43 determining the direction and the position of the coil relative to the patient's head (the patient's brain) based on the information of the marks (the marks disposed on the coil unit and the marks disposed on the patient wearing article or the patient) included in the image photographed by the camera 19; and eddy current density mapping software 43 that calculates an eddy current density induced in the brain based on the direction and the position of the coil determined by the coil position determining software 43 and the coil drive condition determined by the coil drive condition determining software 42 and overlaps the information of the calculated eddy current density with the three-dimensional brain model created by the three-dimensional mapping software to create an eddy current density map (see FIG. 14).

The position and the direction of the coil relative to the patient's brain can be determined by the technique disclosed in WO2007/123147A, for example. In this technique, at least three targets (patient targets) are attached to marks fixed to the patient's head or to equipment for fixing the patient (e.g., a chair or a bed). The positions of the patient targets relative to the patient's head (brain) are determined. Therefore, the positional information of the patient targets is combined with the patient's head tomographic image data (three-dimensional coordinate data). The camera photographs the patient targets and the at least three targets (coil targets) fixed to the coil unit 5. The photographed image is processed by the coil position determining software to obtain the positions and the directions of the coil targets relative to the patient targets and to obtain the position and the direction of the coil relative to the patient's head (brain) based on the information thereof. The position and the direction of the coil relative to the patient's head (brain) are calculated in real time, and the calculated result can be displayed on the display 21.

The operation part 34 has a function of executing the software described above based on an instruction from the CPU 31.

The second storage part 33 stores various data. For example, the stored data include, for example, human (head) tomographic image data 51 and a coil drive condition 52 input through the input part 13, data 53 of the three-dimensional brain model acquired by executing the three-dimensional mapping software 41, data 54 of the coil drive current acquired by executing the coil drive condition determining software 42, data 55 of the direction and the position of the coil acquired by executing the coil position determining software 43, and data 56 of the eddy current density acquired by executing the eddy current density mapping software 43 as well as data 57 for the eddy current map acquired by mapping thereof. The second storage part 33 also stores magnetic stimulation information 58 such as conditions when the magnetic stimulation is applied to the patient's brain by using the system 1 [the current/voltage/frequency applied to the coil, the position and the direction of the coil relative to the head) and the corresponding observed motor threshold (voltage magnitude at which a reaction of muscle is recognized with the probability of 50% or more when a magnetic stimulation is applied to the brain with the coil placed at the optimum stimulation position)].

If a patient is treated by using the system 1 having the above configuration, the position of the coil 8 to the patient's head is obtained by the coil position determining software based on the image photographed by the camera 19. The relative position of the coil 8 to the patient's head is displayed on the display 21. As a result, the coil 8 can be placed at an intended place (e.g., the optimum stimulation position) of the patient's head. Subsequently, the coil drive circuit 25 starts driving based on the coil drive condition input through the input part 15 to apply the magnetic stimulation to the brain of the patient 3. As shown in FIG. 17, the coil drive circuit 25 has a power circuit 62 converting an output voltage of a power source 61 into a desired voltage, a booster circuit 63 boosting an output of the power circuit 62, a capacitor 64 storing an electric charge by utilizing an output from the booster circuit 63, a resistor 65 adjusting a current flowing through the capacitor 64, and a semiconductor switch 66 operating at predetermined timing for the output from the capacitor 64 to form an alternating current, and the current acquired by driving the semiconductor switch 16 based on the output of the CPU 31 is applied to the coil 8.

Figure 19:
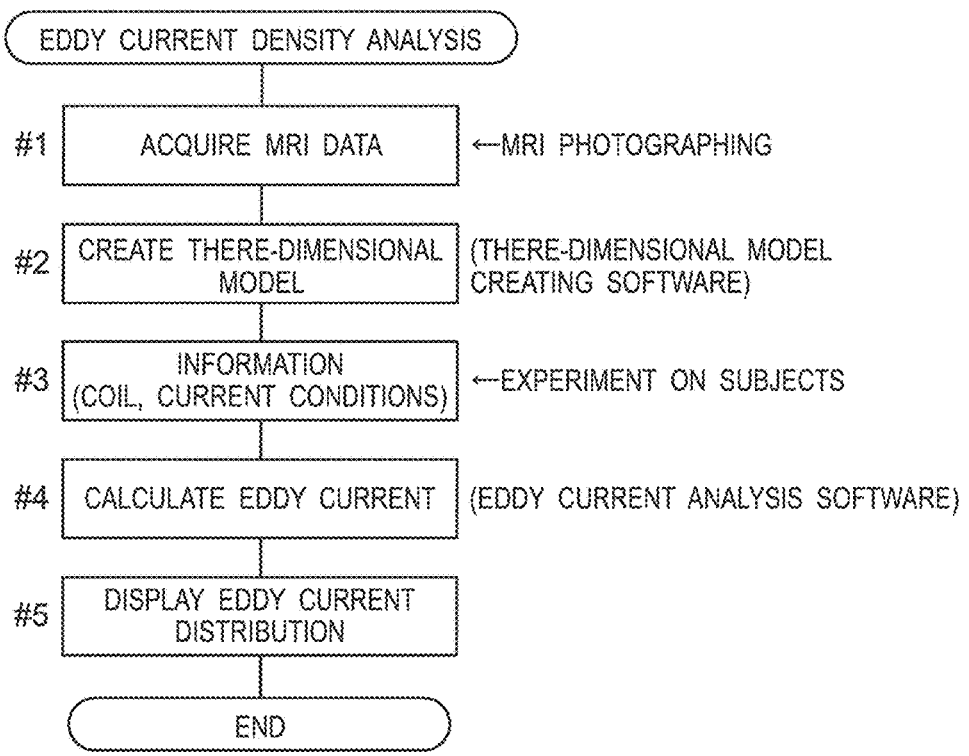
FIG. 19 is a diagram of processes of an eddy current density analysis simulation.

A technique of simulating an eddy current density induced in the patient's brain by using the system 1 will be described in accordance with processes shown in FIG. 19.

Figure 15:
FIG. 15 is a diagram of an analysis result of intracerebral eddy current density induced when the outside of the left prefrontal area is stimulated in a brain model of a subject D.
Figure 20:
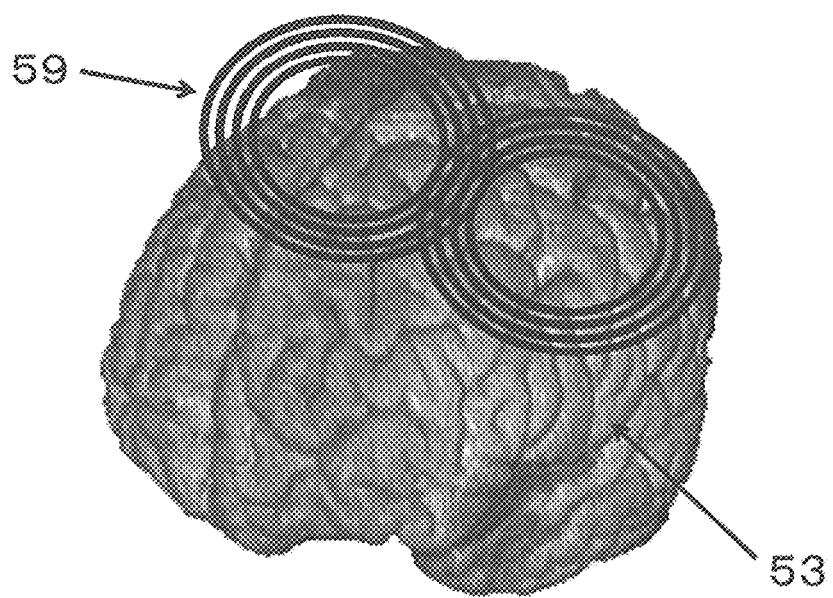
FIG. 20 is a diagram of a three-dimensional brain model as well as a coil winding shape and a coil position.
Figure 21A:
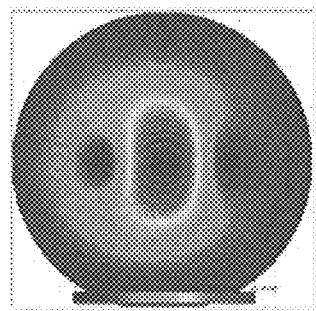
FIG. 21A is a diagram of an induced current of a sphere model of 75 mm in radius generated by a superposed figure-eight coil.
Figure 21B:
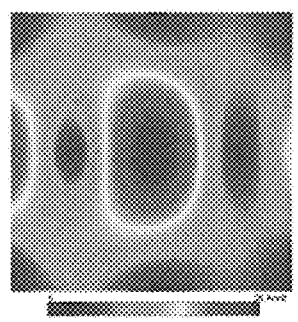
FIG. 21B is a diagram of an eddy current of a cube model of 120 mm in side length induced by the superposed figure-eight coil.
Figure 22A:
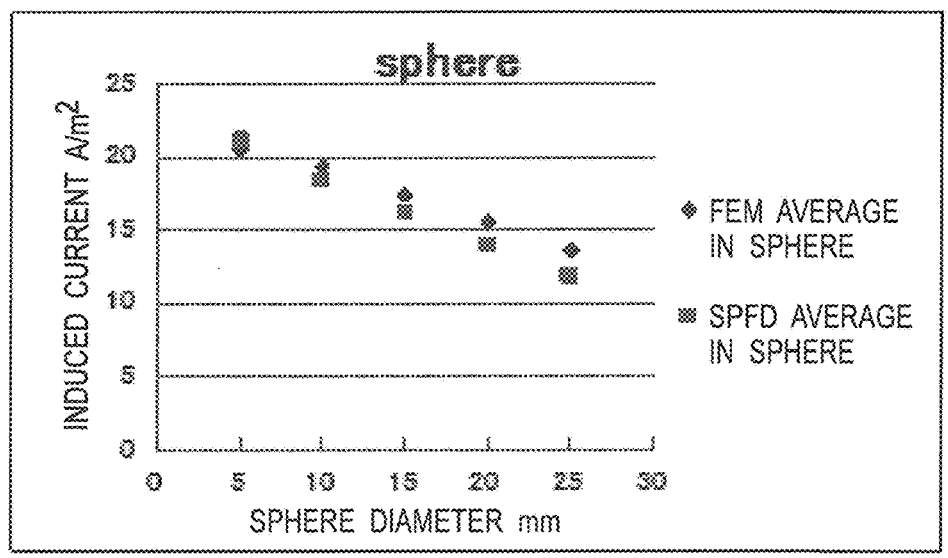
FIG. 22A is a graph of respective average induced current amounts in elements included in a sphere within a constant length from a model surface part of the sphere model of 75 mm in radius calculated by a finite element method and a SPFD method when a current of 5.3 kA and 3.4 kHz is applied to the superposed figure-eight coil at a position 1 cm away from a model surface.
Figure 22B:
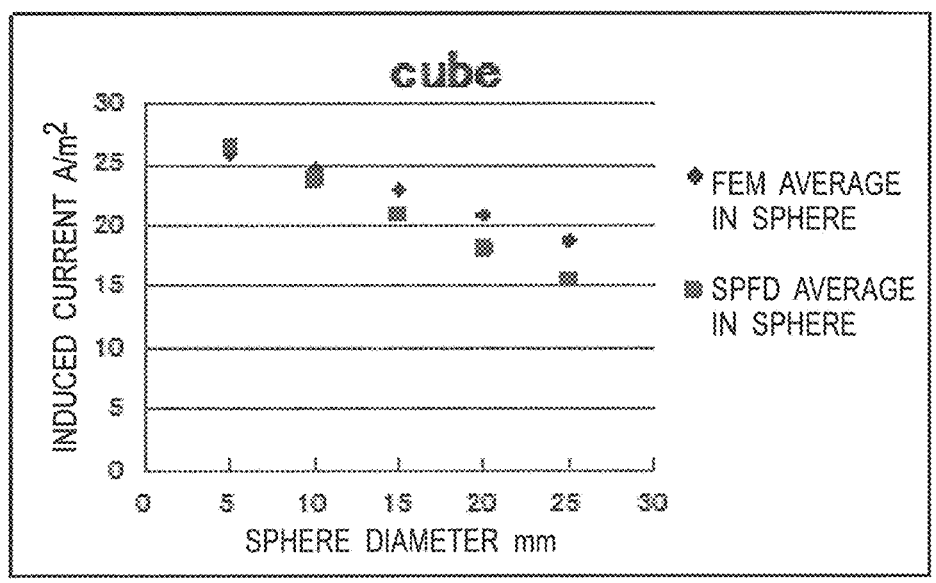
FIG. 22B is a graph of respective average induced current amounts in side length in elements included in a sphere within a constant length from a model surface part of the cube model of 120 mm calculated by a finite element method and a SPFD method when a current of 5.3 kA and 3.4 kHz is applied to the superposed figure-eight coil at a position 1 cm away from a model surface.
Figure 23A:
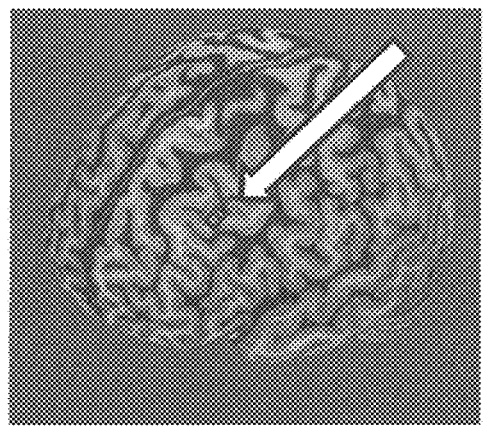
FIG. 23A is a diagram of a head MRI image of a subject.
Figure 23B:
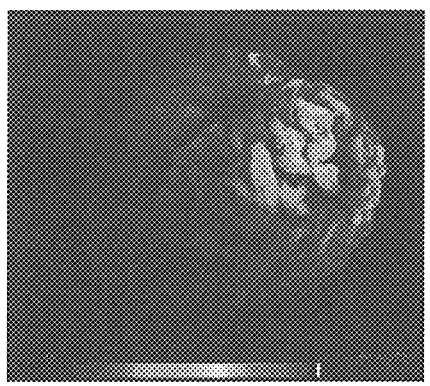
FIG. 23B is a diagram of distribution of currents induced in the brain of FIG. 23A when a predetermined current is applied to a therapeutic coil at a stimulation position that is the primary motor cortex of the brain shown in FIG. 23A.
Figure 23C:
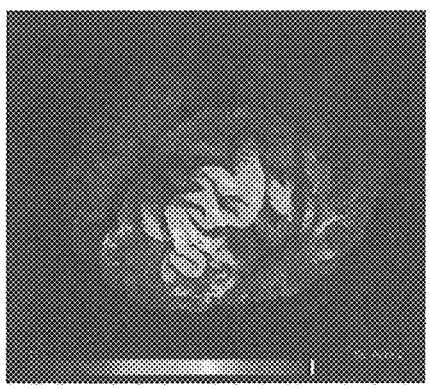
FIG. 23C is a diagram of distribution of currents induced in the brain of FIG. 23A when a predetermined current is applied to a therapeutic coil at a stimulation position that is the prefrontal area of the brain shown in FIG. 23A.
Figure 24A:
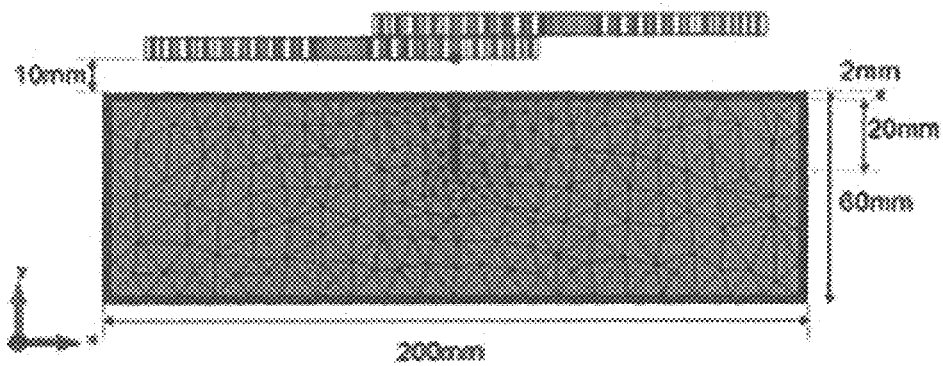
FIG. 24A is a diagram of a simplified brain model including the sulcus.
Figure 24B:
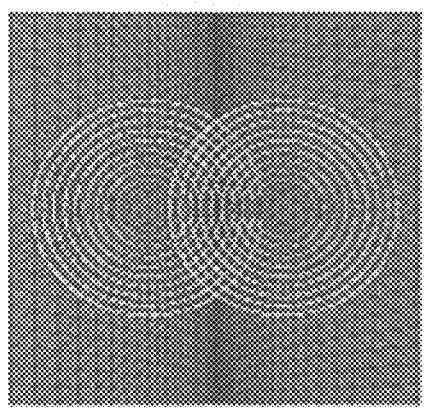
FIG. 24B is a diagram of how induced currents flow when the coil was applied in parallel with the sulcus shown in FIG. 24A.
Figure 24C:
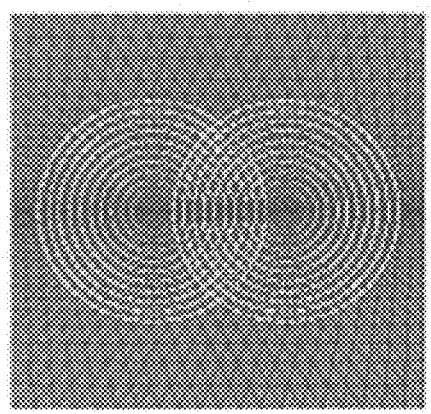
FIG. 24C is a diagram of how induced currents flow when the coil was applied perpendicularly to the sulcus shown in FIG. 24A.
Figure 25A:
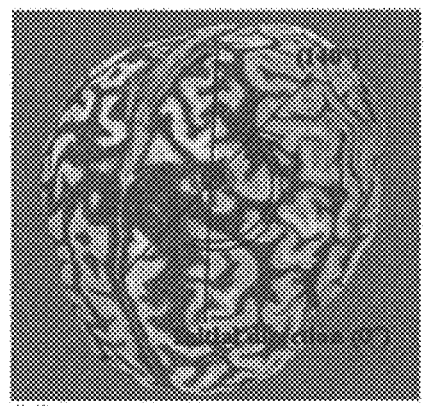
FIG. 25A is a diagram of an actual brain model generated from MRI images of a subject.
Figure 25B:
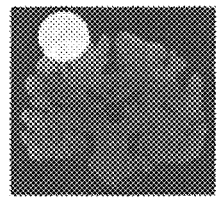
FIG. 25B is a diagram of a sphere for calculating an average of induced currents in the actual brain model shown in FIG. 25A.
Figure 25C:
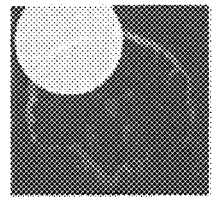
FIG. 25C is a diagram of a sphere for calculating an average of induced currents in a hollow model virtually composed only of the cerebrospinal fluid while having a shape of the actual brain derived from derived from brain MRI images of a patient.
Figure 25D:
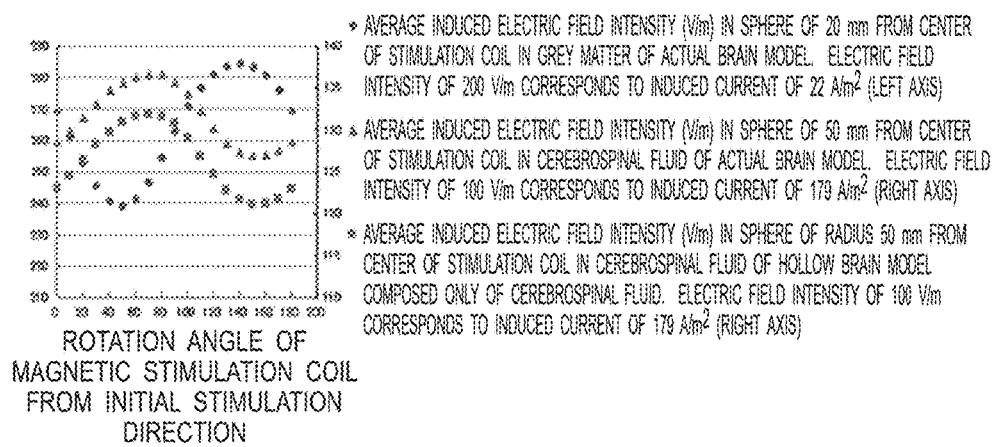
FIG. 25D is a diagram of a relationship between an induced current and a stimulation angle in the grey matter, the white matter, and the cerebrospinal fluid.

First, when the simulation is performed, the head tomographic image data 51 (e.g., MRI data) of the patient 3 or a subject is input through the input part 13 (step #1). The input head tomographic image data 51 is stored in the second storage part 33. Subsequently, based on an instruction from the CPU 31, the three-dimensional brain model 53 of the brain of the patient 3 is created by using the three-dimensional mapping software 41 stored in the first storage part 32 and the head tomographic image data 51 stored in the second storage part 33 (step #2). The three-dimensional brain model 53 created in this case does not have to cover all the sites of the brain and may cover at least any one of the grey matter, the white matter, and the cerebrospinal fluid. The created three-dimensional brain model 53 is stored in the second storage part 33. The three-dimensional brain model can be output and displayed on the display 21 through the output part 14 as needed. Subsequently, the CPU 31 reads the magnetic stimulation information 58 acquired and stored in the second storage part 33 when a magnetic stimulation was previously applied to the head of the patient 3 by using the system 1 [the current/voltage/frequency applied to the coil, the position and the direction of the coil relative to the head) and winding shape data 59 of the coil (see FIG. 20), as well as the corresponding observed motor threshold (voltage magnitude at which a reaction of muscle is recognized with the probability of 50% or more when a magnetic stimulation is applied to the brain with the coil placed at the optimum stimulation position)] (step #3). The CPU 31 reads the eddy current density mapping software 43 stored in the first storage part 32 and the three-dimensional brain model 53 of the brain stored in the second storage part 33 and calculates an eddy current density induced in each of minute polyhedral units of the three-dimensional brain model with reference to the magnetic stimulation information 58 by using the eddy current density mapping software 43 (step #4). This calculation is performed by the scalar potential finite difference method described above. The data 56 of the calculated eddy current density is stored in the second storage part 33. Lastly, the CPU 31 creates an eddy current density map 57 (see FIG. 14) based on the data 56 of the calculated eddy current density. As shown in FIG. 15, preferably, color information is added to the data 56 of the calculated eddy current density in accordance with the level thereof to display the level of the eddy current density with this color information on the display 21.

In addition to the above described form of calculating and displaying the eddy current density by using the magnetic stimulation information 58 acquired and stored in the second storage part 33 when a magnetic stimulation was previously applied to the head of the patient 3 by using the system 1 [the current/voltage/frequency applied to the coil, the position and the direction of the coil relative to the head), the simulation method according to the present invention may be used in the form of calculating the eddy current density distribution in the entire brain viewed from above or the eddy current density at a certain intracerebral position in the case of changing a position of a therapeutic coil to which setting is input by using a predetermined setting means, and the simulation method according to the present invention described earlier may additionally or independently be used for calculating the eddy current density distribution in the entire brain viewed from above or the eddy current density at a certain intracerebral position in the case of changing at least any of information on coil direction, information on coil applied current, and information on applied voltage. The eddy current density at a certain intracerebral position can be displayed in real time in accordance with movement of the coil. It is noted that pluralities of simulation results and conditions can be displayed at the same time on the display 21 so as to compare and observe these results and conditions.

As described above, according to the present invention, by calculating the eddy current density for the three-dimensional brain model reproducing the patient's brain to create the eddy current density map based on the magnetic stimulation information acquired by actually stimulating the patient's brain, it can be confirmed what level of the eddy current is induced in what part of the stimulated patient's brain and what amount of the induced eddy current causes a reaction (e.g., twitch) to appear on the patient.

EXPLANATIONS OF LETTERS OR NUMERALS

1 transcranial magnetic stimulation system
2 chair
3 patient
4 magnetic stimulation device
5 coil unit (coil device)
6 control unit
7 positioning unit
8 coil
9 casing
10 holder
11 mark
12 housing
13 input part
14 output part
19 camera
30 control circuit

The invention claimed is:

1. An intracerebral current simulation method comprising:
a first step of providing head image data including at least a portion of a brain out of tomographic image data of a patient;
a second step of forming a three-dimensional brain model composed of respective minute polyhedral units acquired by dividing at least one region making up the brain of the head image data provided at the first step into minute elements;
a third step of providing first information including, out of conditions when a coil is placed on the head of the patient to apply a current to the coil to provide a magnetic stimulation to the brain of the patient and a patient's reaction to the magnetic stimulation is observed, at least conditions of a position and a direction of the coil, a condition of the current applied to the coil, and a condition of structure related to a formed magnetic field of the coil; and
a fourth step of calculating eddy currents or electric fields induced in the respective minute polyhedral units of the three-dimensional brain model based on the first information provided at the third step and second information including an electric conductivity assigned to each of the minute polyhedral unit,
wherein the three-dimensional brain model is a model comprising data of at least one of cerebrospinal fluid, grey matter, and white matter, except for skins and muscles.

2. The intracerebral current simulation method according to claim 1, comprising a fifth step of visually displaying distribution of the eddy currents or electric fields calculated at the fourth step.

3. The intracerebral current simulation method according to claim 1, wherein the first information includes at least a current value or a voltage value of the current.

4. The intracerebral current simulation method according to claim 1, wherein at the fourth step, the eddy currents or electric fields are calculated by a scalar potential finite difference method.

5. The intracerebral current simulation method according to claim 1, wherein the current applied to the coil is an alternating current or a pulsating current.

6. The intracerebral current simulation method according to claim 1, wherein the three-dimensional brain model is a model consisting of the cerebrospinal fluid, the grey matter or the white matter.

7. The intracerebral current simulation method according to claim 1, wherein the three-dimensional brain model is a model consisting of the cerebrospinal fluid, the grey matter and the white matter.

8. The intracerebral current simulation method according to claim 1, wherein the cerebrospinal fluid is assigned to have an electric conductivity that is greater than that of the grey matter or the white matter.

9. The intracerebral current simulation method according to claim 1, wherein the three-dimensional brain model is a model consisting of data of the cerebrospinal fluid.

10. An intracerebral current simulation device comprising:
a first means configured to provide head image data including at least a portion of a brain out of tomographic image data of a patient;
a second means configured to form a three-dimensional brain model composed of respective minute polyhedral units acquired by dividing at least one region making up the brain of the head image data provided by the first means into minute elements;
a third means configured to provide first information including, out of conditions when a coil is placed on the head of the patient to apply a current to the coil to provide a magnetic stimulation to the brain of the patient and a patient's reaction to the magnetic stimulation is observed, at least conditions of a position and a direction of the coil, a condition of the current applied to the coil, and a condition of structure related to a formed magnetic field of the coil; and a fourth means configured to calculate eddy currents or electric fields induced in the respective minute polyhedral units of the three-dimensional brain model based on the first information provided by the third means and second information including an electric conductivity assigned to each of the minute polyhedral units,
wherein the three-dimensional brain model is a model comprising data of at least one of cerebrospinal fluid, grey matter, and white matter, except for skins and muscles.

11. The intracerebral current simulation device according to claim 10, comprising a fifth means visually displaying distribution of the eddy currents calculated by the fourth means.

12. The intracerebral current simulation device according to claim 10, wherein the first information includes at least a current value or a voltage value of the current.

13. The intracerebral current simulation device according to claim 10, wherein in the fourth means, the eddy currents or electric fields are calculated by a scalar potential finite difference method.

14. The intracerebral current simulation device according to claim 10, wherein the current applied to the coil is an alternating current or a pulsating current.

15. A transcranial magnetic stimulation system comprising: the intracerebral current simulation device according to claim 10.

16. An intracerebral current simulation device comprising:
a first means for providing head image data including at least a portion of a brain out of tomographic image data of a patient;
a second means for forming a three-dimensional brain model composed of respective minute polyhedral units acquired by dividing at least one region making up the brain of the head image data provided by the first means into minute elements;
a third means for providing first information including, out of conditions when a coil is placed on the head of the patient to apply a current to the coil to provide a magnetic stimulation to the brain of the patient, at least conditions of a position and a direction of the coil, a condition of the current applied to the coil, and a condition of structure related to a formed magnetic field of the coil; and
a fourth means for calculating eddy currents or electric fields induced in the respective minute polyhedral units of the three-dimensional brain model based on the first information provided by the third means and second information including an electric conductivity assigned to each of the minute polyhedral units,
wherein the three-dimensional brain model is a model comprising data of at least one of cerebrospinal fluid, grey matter, and white matter, except for skins and muscles.

17. The intracerebral current simulation device according to claim 16, comprising a fifth means for visually displaying distribution of the eddy currents or electric fields calculated by the fourth means.

18. The intracerebral current simulation device according to claim 16, wherein the first information includes at least a current value or a voltage value of the current.

19. The intracerebral current simulation device according to claim 16, wherein in the fourth means, the eddy currents or electric fields are calculated by a scalar potential finite difference method.

20. The intracerebral current simulation device according to claim 16, wherein the current applied to the coil is an alternating current or a pulsating current.

21. A transcranial magnetic stimulation system comprising: the intracerebral current simulation device according to claim 16.

22. The intracerebral current simulation device according to claim 16, wherein the three-dimensional brain model is a model consisting of data of the cerebrospinal fluid, the grey matter and the white matter.

23. The intracerebral current simulation device according to claim 16, wherein the three-dimensional brain model is a model consisting of data of the cerebrospinal fluid.

* * * * *